(12) United States Patent
Pfeiffer et al.

(10) Patent No.: US 10,137,386 B2
(45) Date of Patent: *Nov. 27, 2018

(54) SEPARATION OF IONIC LIQUIDS IN COALESCING DEVICES

(71) Applicant: BASF SE, Ludwigshafen (DE)

(72) Inventors: Daniel Pfeiffer, Neustadt (DE); Stefan Bitterlich, Dirmstein (DE); Michael Hübner, Weinheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/039,084

(22) PCT Filed: Dec. 1, 2014

(86) PCT No.: PCT/EP2014/076072
§ 371 (c)(1),
(2) Date: May 25, 2016

(87) PCT Pub. No.: WO2015/082388
PCT Pub. Date: Jun. 11, 2015

(65) Prior Publication Data
US 2017/0157537 A1 Jun. 8, 2017

(30) Foreign Application Priority Data

Dec. 2, 2013 (EP) .................................. 13195321

(51) Int. Cl.
*C07C 7/144* (2006.01)
*B01D 17/04* (2006.01)
(Continued)

(52) U.S. Cl.
CPC ........... *B01D 17/045* (2013.01); *B01D 17/08* (2013.01); *B01D 17/10* (2013.01); *C07C 7/005* (2013.01)

(58) Field of Classification Search
CPC .............................. C07C 7/005; B01D 17/045
(Continued)

(56) References Cited

U.S. PATENT DOCUMENTS 9,095,789 B2 8/2015 Pfeiffer et al.
9,352,896 B2 5/2016 Deutsch
(Continued)

FOREIGN PATENT DOCUMENTS

WO WO-2010062922 A2 6/2010
WO WO-2011069929 A1 6/2011
(Continued)

OTHER PUBLICATIONS

International Search Report for PCT/EP2014/076072 dated May 26, 2015.
(Continued)

*Primary Examiner* — Philip Y Louie
*Assistant Examiner* — Aaron W Pierpont
(74) *Attorney, Agent, or Firm* — Drinker Biddle & Reath LLP

(57) ABSTRACT

A process for separating a phase (A) comprising at least one ionic liquid from a phase (B), where phase (A) has a higher viscosity than phase (B), comprising: a) providing a stream (S1) comprising a dispersion (D1) in which phase (A) is dispersed in phase (B), b) introducing stream (S1) into a coalescing device (KV), where the inflow rate of stream (S1) is from 0.05 to 150 kg/(cm$^2$*h) based on the average cross-sectional area of coalescing device (KV), wherein the packing density of coalescing device (KV) is from 50 to 500 kg/m$^3$, separating phase (A) from phase (B) in coalescing device (KV), discharging a stream (S2) comprising at least 70% by weight of phase (A) from coalescing device (KV) and discharging a stream (S3) comprising at least 70% by weight of phase (B) from coalescing device (KV).

25 Claims, 1 Drawing Sheet

(51) Int. Cl.
*B01D 17/00* (2006.01)
*C07C 7/00* (2006.01)

(58) Field of Classification Search
USPC ........................................ 585/803, 818, 800
See application file for complete search history.

(56) References Cited

U.S. PATENT DOCUMENTS

| | | | |
|---|---|---|---|
| 9,409,839 B2 | 8/2016 | Pfeiffer et al. | |
| 2007/0299294 A1* | 12/2007 | Lin ........................... | C07C 5/10 585/857 |
| 2008/0269426 A1* | 10/2008 | Bitterlich ................. | B01D 3/14 525/378 |
| 2010/0130800 A1* | 5/2010 | Luo ....................... | B01D 17/045 585/446 |
| 2010/0200512 A1* | 8/2010 | Chase ................... | B01D 17/045 210/708 |
| 2011/0137098 A1* | 6/2011 | Tschirschwitz ....... | C07C 5/2789 585/374 |
| 2014/0014596 A1 | 1/2014 | Pfeiffer et al. | |
| 2014/0018588 A1 | 1/2014 | Spuhl et al. | |
| 2014/0018590 A1 | 1/2014 | Tschirschwitz et al. | |
| 2014/0018591 A1 | 1/2014 | Tschirschwitz et al. | |
| 2014/0018595 A1 | 1/2014 | Spuhl et al. | |
| 2014/0018596 A1* | 1/2014 | Pfeiffer ................... | C07C 7/144 585/803 |
| 2014/0018597 A1 | 1/2014 | Pfeiffer et al. | |
| 2014/0024875 A1 | 1/2014 | Spuhl et al. | |
| 2014/0114099 A1 | 4/2014 | Tschirschwitz et al. | |
| 2014/0114100 A1 | 4/2014 | Tschirschwitz et al. | |
| 2014/0114103 A1 | 4/2014 | Schmitt et al. | |
| 2014/0128648 A1 | 5/2014 | Prochazka et al. | |
| 2014/0257003 A1 | 9/2014 | Tschirschwitz et al. | |

FOREIGN PATENT DOCUMENTS

| | | |
|---|---|---|
| WO | WO-2012104769 A1 | 8/2012 |
| WO | WO-2014/009335 A1 | 1/2014 |
| WO | WO-2014/009353 A1 | 1/2014 |

OTHER PUBLICATIONS

English Translation of International Prelminary Report on Patentability for application PCT/EP2014/076072, dated Jan. 2015.
Wines, T., et al., "Chemical Engneering—Difficult Liquid-Liquid Separations", 1997, pp. 104-109.

* cited by examiner

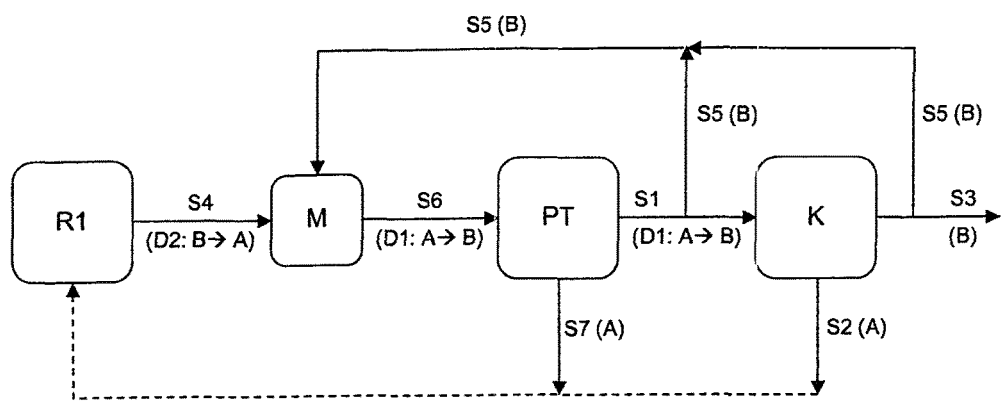

SEPARATION OF IONIC LIQUIDS IN COALESCING DEVICES

CROSS-REFERENCE TO RELATED APPLICATIONS

This application is a national stage application (under 35 U.S.C. § 371) of PCT/EP2014/076072, filed Dec. 1, 2014, which claims benefit of European Application No. 13195321.8, filed Dec. 2, 2013, both of which are incorporated herein by reference in their entirety.

The present invention relates to a process for separating a phase (A) comprising at least one ionic liquid from a phase (B) in a coalescing device (KV), where the phase (A) has a higher viscosity than the phase (B). Here, a stream (S1) comprising a dispersion (D1) in which the phase (A) is dispersed in the phase (B) is introduced at an inflow rate of from 0.05 to 150 kg/(cm$^2$*h) into the coalescing device (KV). The coalescing device (KV) is preferably a coalescing filter or a knitted fabric; two or more coalescing devices (KV) can optionally also be connected in series or preferably in parallel.

Ionic liquids are, inter alia, suitable as catalysts for the isomerization of hydrocarbons. Such a use of an ionic liquid is disclosed, for example, in WO 2011/069929 where a specific selection of ionic liquids is used in the presence of an olefin for the isomerization of saturated hydrocarbons, in particular for the isomerization of methylcyclopentane (MCP) to cyclohexane.

In general, ionic liquids on the one hand and hydrocarbons (or organic phases in general) on the other hand are immiscible or can be mixed only with great difficulty: they form two separate phases. To be able to utilize the above-mentioned catalysis effect, intimate contact between organic phase and the ionic liquid has to be established. For this purpose, the two phases are frequently mixed in stirred tanks with vigorous stirring to give dispersions. Depending on parameters such as the type of ionic liquid or of the organic phase or the phase ratio, the dispersion can either be present as a dispersion of an ionic liquid in the organic phase or as a dispersion of the organic phase in the ionic liquid. Regardless of the specific dispersing direction present, separating the disperse phase from the continuous phase after the reaction is a general problem associated with such dispersions. Cases in which the ionic liquid in the form of very fine droplets (d<900 μm) is to be separated off from a dispersion in which the ionic liquid is dispersed in the organic phase (ultrafine droplet problem) are particularly problematic.

To separate two-phase or multiphase mixtures, in particular dispersions, the use of coalescing filters has long been known. For example, WO 2012/104769 discloses a method of reducing the water content in pyrolysis gasoline using a coalescing filter made of metal and/or glass fibers. However, a coalescing filter can not only be used for separating water from mixtures (dispersions) with an organic phase (pyrolysis gasoline) but also for separating ionic liquids from dispersions with an organic phase.

WO 2010/062922 discloses a multistage process for separating an ionic liquid from hydrocarbons using a coalescing filter. The coalescing filter material has to be such that it has a greater affinity for the ionic liquid than for the hydrocarbons. According to WO 2010/062922, suitable coalescing filter materials are glass beads, stainless steel, glass fibers, polymer fibers or organic membranes, in particular glass fibers. A separation of the ionic liquid from the hydrocarbons is effected in the coalescing filter.

The international application PCT/EP 2013/064459 (filed on Jul. 9, 2013) relates to a process for separating a phase (A) comprising at least one ionic liquid from a phase (B) in a coalescing filter made of acrylic-phenolic resin. The phase (A) has a higher viscosity than the phase (B) which, for example, comprises a hydrocarbon such as cyclohexane. In this process, a dispersion (D1) in which the phase (A) is dispersed in the phase (B) is introduced as constituent of a stream (S1) into the corresponding coalescing filter. An analogous process is disclosed in the international patent application PCT/EP 2013/064432 (filed on Jul. 9, 2013). In this process, the separation of the phase (A) from the phase (B) is carried out using a phase separation unit comprising a knitted fabric instead of using a coalescing filter made of acrylic-phenolic resin (as per PCT/EP 2013/064459).

However, nowhere does the prior art state the rate at which the dispersion in which, for example, an ionic liquid (phase (A)) is dispersed in a hydrocarbon (phase (B)) impinges on the coalescing device, for example a coalescing filter or a knitted fabric.

It is an object of the present invention to provide a novel process for separating an ionic liquid from an organic phase, where the ionic liquid is dispersed in the organic phase.

The object is achieved by a process for separating a phase (A) comprising at least one ionic liquid from a phase (B), where the phase (A) has a higher viscosity than the phase (B), which comprises the following steps:
 a) provision of a stream (S1) comprising a dispersion (D1) in which the phase (A) is dispersed in the phase (B),
 b) introduction of the stream (S1) into a coalescing device (KV), where the inflow rate of the stream (S1) is from 0.05 to 150 kg/(cm$^2$*h) based on the average cross-sectional area of the coalescing device (KV),
 c) separation of the disperse phase (A) from the phase (B) in the coalescing device (KV),
 d) discharge of a stream (S2) comprising at least 70% by weight, preferably at least 90% by weight, of phase (A) from the coalescing device (KV) and
 e) discharge of a stream (S3) comprising at least 70% by weight, preferably at least 90% by weight, of phase (B) from the coalescing device (KV).

The process of the invention makes it possible to achieve effective separation of ionic liquids from dispersions with organic phases, in particular from dispersions with hydrocarbons, in an advantageous way. According to the invention, the problem of, in particular, separating off ionic liquid present in finely disperse form and/or in small amounts in a dispersion with an organic phase (ultrafine droplet problem) can be solved.

The process of the invention also enables relatively small amounts (<1% by weight) of ionic liquid to be separated off from a dispersion with an organic phase, in particular with a hydrocarbon phase; this also applies, in particular, when a dispersing direction of ionic liquid in organic phase is present. Control of the dispersing direction of phase (A; ionic liquid) in phase (B; organic phase) enables a high (fast) separation rate to be achieved, with the consequence that the size of the phase separators used in the process can be significantly reduced compared to the case of the reverse dispersing direction—phase (B; organic phase) in phase (A; ionic liquid).

The process of the invention can thus be carried out independently of the dispersing direction present in the preceding process steps. If, for example, a dispersing direction with phase (B) in phase (A) is present in a preceding isomerization step because, for example, a significant excess of ionic liquid is used in the isomerization, inversion of the dispersing direction can be carried out without any problem in a preferred embodiment of the present invention. The inversion of the dispersing direction is, according to the invention, carried out by recirculating a stream comprising an excess of organic phase to upstream of the coalescing device (KV), for example upstream of a coalescing filter made of acrylic-phenolic resin, and in particular also upstream of an additional phase separator located upstream of the coalescing device (KV).

Owing to the setting of the inflow rate of the stream (S1) comprising the dispersion (D1) to values of from 0.05 to 150 kg/(cm$^2$*h) on introduction into the coalescing device (KV), where the abovementioned values of the inflow rate of the stream (S1) are based on the average cross-sectional area of the coalescing device (KV), the above-described ultrafine droplet problem can be eliminated particularly efficiently by means of the process of the invention. As coalescing devices (KV), it is in principle possible to use all coalescing devices known to those skilled in the art, with preference being given for this purpose to coalescing filters or knitted fabrics, in particular coalescing filters.

For the purposes of the present invention, a coalescing device (KV) is any device in which a coalescence-based separation of two phases can be carried out. The coalescing device (KV) itself can in turn be a constituent of a larger device/apparatus, for example an apparatus in which a coalescing device (KV), for example a coalescing filter or a knitted fabric, and also further devices can be present, in which case these further devices may likewise be suitable for separating liquids but are based on a separation mechanism other than coalescence. These further devices can, for example, be conventional filters or prefilters.

The physical mechanism of any separation based on coalescence is described, for example, in the article by T. Wines et al. (Chemical Engineering; December 1997; pages 104 to 109) in connection with coalescing filters. However, this separation mechanism is not restricted to the use of coalescing filters but applies equally to the use of knitted fabrics or other materials. In a coalescence-based separation, there is initially adhesion of the dispersed droplets comprised in the continuous phase to the surface of the coalescing device (KV), i.e. the coalescing material as such, for example a coalescing filter made of acrylic-phenolic resin. The droplets caught by the coalescing device coalesce in the form of droplet growth on this surface. The droplets which have grown as a result of the coalescence process subsequently drop off or settle out, as a result of which phase separation is achieved.

The effect achieved by the control of the inflow rate of the dispersion (D1) can be improved further when the coalescing device (KV) has a specific packing density in the range from 50 to 500 kg/m$^3$. Likewise, a further improvement can be observed when the process of the invention is carried out using not only one coalescing device (KV) but instead two or more coalescing devices (KV), for example in a parallel or series arrangement with appropriate coalescing devices.

If a coalescing filter is used as coalescing device (KV), a further improvement in the process can be achieved when the pressure drop over the coalescing filter is in the range from 0.001 to 1 bar and/or a solids filter without adhesion is used.

If coalescing filters made of acrylic-phenolic resin are used as coalescing device (KV), these are additionally more stable (under the boundary conditions relevant to the present process) compared to other coalescing filters (for example polyphenylene sulfide) and/or maintain their (separation) performance (coalescing action) over a longer period of time.

The process of the invention for separating off ionic liquids in coalescing devices will be defined in more detail below.

The phase (A) comprises at least one ionic liquid. For example, mixtures of two or more ionic liquids can be comprised in the phase (A); the phase (A) preferably comprises one ionic liquid. Apart from the ionic liquid, the phase (A) can also comprise further components which are miscible with the ionic liquid. Such components can be, for example, cocatalysts which are employed in isomerization reactions using ionic liquids. A preferred example of such cocatalysts is hydrogen halides, in particular hydrogen chloride. Furthermore, constituents or decomposition products of the ionic liquids, which can be formed, for example, in the reaction catalyzed by the ionic liquid, such as aluminum chloride, can also be comprised in the phase (A). The proportion of ionic liquid in the phase (A) is preferably greater than 80% by weight (based on the sum of all components of the phase (A)).

Ionic liquids suitable for the purposes of the present invention are in principle all ionic liquids known to those skilled in the art as long as they catalyze the reaction to be carried out, e.g. isomerization. An overview of ionic liquids suitable for catalyzing isomerization reactions may be found, for example, in WO 2011/069929. For the purposes of the present invention, an acidic ionic liquid is preferred. The ionic liquid comprised in the phase (A) is preferably an acidic ionic liquid having the composition $K1Al_nX_{(3n+1)}$, where K1 is a monovalent cation, X is halogen and $1<n<2.5$. K1 is preferably an unsubstituted or at least partially alkylated ammonium ion or a heterocyclic (monovalent) cation, in particular a pyridinium ion, an imidazolium ion, a pyridazinium ion, a pyrazolium ion, an imidazolinium ion, a thiazolium ion, a triazolium ion, a pyrrolidinium ion, an imidazolidinium ion or a phosphonium ion. X is preferably chlorine or bromine.

The acidic ionic liquid more preferably comprises an at least partially alkylated ammonium ion or a heterocyclic cation as cation and/or a chloroaluminate ion having the composition $Al_nCl_{(3n+1)}$ where $1<n<2.5$ as anion. The at least partially alkylated ammonium ion preferably comprises one, two or three alkyl radicals (each) having from 1 to 10 carbon atoms. If two or three alkyl substituents are present on the corresponding ammonium ions, the chain length in each case can be selected independently; preference is given to all alkyl substituents having the same chain length. Particular preference is given to trialkylated ammonium ions having a chain length of from 1 to 3 carbon atoms. The heterocyclic cation is preferably an imidazolium ion or a pyridinium ion.

The acidic ionic liquid particularly preferably comprises an at least partially alkylated ammonium ion as cation and a chloroaluminate ion having the composition $Al_nCl_{(3n+1)}$ where $1<n<2.5$ as anion. Examples of such particularly preferred ionic liquids are trimethylammonium chloroaluminate and triethylammonium chloroaluminate.

For the purposes of the present invention, the phase (A) has a higher viscosity than the phase (B). The phase (A) preferably has a viscosity which is at least 0.1 mPas, in particular at least 20 mPas, higher than that of the phase (B).

A first characteristic feature of the phase (B) is, for the purposes of the present invention, that it has a lower viscosity than the phase (A). The phase (B) can, for example, be an organic phase. The phase (B) preferably comprises at least one hydrocarbon. The phase (B) more preferably comprises, as hydrocarbon, cyclohexane or a mixture of cyclohexane with at least one further hydrocarbon selected from among methylcyclopentane (MCP), n-hexane, isohexane, n-heptane, isoheptane and dimethylcyclopentane. The phase (B) particularly preferably comprises a mixture of cyclohexane, MCP and at least one further hydrocarbon.

In the context of the present invention, a stream (S1) comprising a dispersion (D1) in which the phase (A) is dispersed in the phase (B) is provided in step a). The dispersing direction (i.e. the information as to which phase is present in disperse form in the respective other phase) can be determined by examining a sample, optionally after addition of a dye which selectively colors one phase, under an optical microscope using transmitted light.

The dispersion (D1) can be produced by methods known to those skilled in the art; for example, such a dispersion can be produced by vigorous stirring of the components comprised in the respective phases. Such a procedure can, for example, take place in a hydrocarbon isomerization process using an ionic liquid. The dispersion (D1) is (as explained in more detail below) preferably taken off as upper phase from a phase separation apparatus which is particularly preferably located downstream of an apparatus in which a reaction catalyzed by the ionic liquid is carried out and in which the ionic liquid and the organic phase are brought into contact with stirring. The phases (A) and (B) can be present in any ratios to one another in the dispersion (D1) as long as the phase (A) is dispersed in the phase (B). The dispersion (D1) in the stream (S1) preferably comprises a maximum of 10% by weight, in particular a maximum of 5% by weight, of the phase (A) (in each case based on the amount of phase (B)).

In step b according to the invention, the steam (S1) is introduced into a coalescing device (KV), where the inflow rate of the stream (S1) is from 0.05 to 150 kg/(cm$^2$*h) based on the average cross-sectional area of the coalescing device (KV).

Coalescing devices (KV) are known per se to those skilled in the art. For the purposes of the present invention, it is in principle possible to use all coalescing devices (KV) which are suitable for separating the phase (A) from the phase (B) in a dispersion (D1) in which the phase (A) is dispersed in the phase (B). The separation is preferably effected to completion or at least in large portions, i.e. at least 70% by weight, preferably 90% by weight, in particular at least 99% by weight, of the phase (A) comprised in the dispersion (D1) are, according to the invention, separated off using the coalescing device (KV). Preference is given to using a coalescing filter or a knitted fabric, in particular a coalescing filter, as coalescing device (KV).

Furthermore, it is also possible to use two or more coalescing devices (KV), in particular coalescing filters, in the process of the invention and it is also conceivable to employ a combination of different coalescing devices (KV), for example a combination of two or more different coalescing filters made of glass fibers and stainless steel or combinations of at least one knitted fabric and at least one coalescing filter, where the respective knitted fabrics and/or coalescing filters can likewise be different.

Coalescing filters can, according to the invention, be made of all filter materials known to those skilled in the art which are suitable for carrying out a separation based on coalescence. Such coalescing filters are frequently configured as candles (referred to as coalescing candles) and can optionally be integrated into a larger unit, for example in a filter vessel.

Coalescing filters can be made entirely or at least partially of glass beads, metals, fiberglass (glass fibers), polymer fibers or ceramic membranes or else mixtures thereof. Metals can be present as metal packings, with preference being given to stainless steel as metal. Preferred polymer fibers are fibers made of acrylic-phenolic resin.

Coalescing filters which are preferred for the purposes of the present invention are those which are made of acrylic-phenolic resin and glass fibers, particularly preferably of acrylic-phenolic resin.

Such coalescing filters are known to those skilled in the art and are, for example, commercially available from Fuhr GmbH (Germany) or from the manufacturer CUNO Fluid Purification. Such suitable coalescing filters have finenesses of 1-150 µm, preferably 10, 25 or 50 µm, particularly preferably 10 µm. Furthermore, two versions in respect of the surface are possible: grooved and ungrooved, preference is given to ungrooved. The candles of the coalescing filter as such have, for example, an internal diameter of 27 mm and an external diameter of 65 mm and are obtainable in lengths of from 4" to 60". The candle is preferably an unsymmetrical, resin-bonded filter candle without a support core. It preferably comprises essentially acrylic fibers bonded by means of phenolic resin.

As already mentioned above, the coalescing filter can be integrated into a larger unit, for example a filter vessel. For the purposes of the present invention, a coalescing filter which is made, for example, of acrylic-phenolic resin, is the filter material as such. The other components of the filter unit, for example the vessel of the unit (filter vessel) or the filter module in which the filter material is accommodated, can be made of materials other than, for example, acrylic-phenolic resin.

The term "made of" means, for the purposes of the present invention, that the material used for producing the filter material comprises acrylic-phenolic resin. The filter material preferably comprises at least 50% by weight, more preferably at least 75% by weight and in particular at least 95% by weight, of acrylic-phenolic resin. The above values are given by way of example for acrylic-phenolic resin and apply analogously to all other filter materials, for example those composed of metal or glass fibers.

If a knitted fabric is used according to the invention for a coalescing device (KV), it is preferably a glass fiber knit.

Suitable knitted fabrics, in particular glass fiber knits, are known to those skilled in the art and are commercially available from, for example, Rhodius (Germany). The preferred glass fiber knits are glass staple fibers having a fiber diameter in the range from 0.1 to 0.6 mm, preferably from 0.14 to 0.3 mm. The knitted fabric comprises essentially rolled-up (glass staple) fiber mats having a packing density in the range from 100 to 800 kg/m$^3$, preferably from 150 to 500 kg/m$^3$, particularly preferably from 200 to 400 kg/m$^3$.

As indicated analogously above for the coalescing filters, such a knitted fabric is usually integrated into a larger apparatus, for example a phase separation unit. The phase separation unit comprising a knitted fabric is preferably a phase separator, particularly preferably a downstream phase separator, i.e. an apparatus which is positioned upstream of a further phase separator.

The inflow rate of the stream (S1) in step b) is preferably from 0.5 to 20 kg/(cm$^2$*h), in particular from 0.5 to 5 kg/(cm$^2$*h), based on the average cross-sectional area of the coalescing device (KV). Preference is given to using coalescing filters here. If a coalescing filter is used, all ranges indicated above (including the range from 0.05 to 150 kg/(cm$^2$*h)) are based on the cross-sectional area of the coalescing filter.

Furthermore, preference is given to the packing density of the coalescing device (KV) being from 50 to 500 kg/m$^3$ and/or at least two coalescing devices (KV) being connected in parallel, with the at least two coalescing devices (KV) being operable simultaneously and/or alternately.

If a coalescing filter is used as coalescing device (KV) in the process of the invention, preference is given to the coalescing filter being used without adhesive bonding and/or the pressure drop over the coalescing filter being from 0.001 to 1 bar, preferably from 0.001 to 0.5 bar, particularly preferably from 0.001 to 0.2 bar.

In step c), the disperse phase (A) is separated from the phase (B) in the coalescing device (KV). The way in which the separation as such is carried out, giving separate phases (A) and (B) as a result of the coalescing effect of the coalescing device (KV), by means of a coalescing device (KV), in particular by means of a coalescing filter, is known to those skilled in the art.

In step d) of the process of the invention, a stream (S2) comprising at least 70% by weight, preferably at least 90% by weight, of phase (A) is discharged from the coalescing device (KV). The stream (S2) particularly preferably does not comprise any phase (B) or comprises only a small amount (<1% by weight) of phase (B). The above figures in % by weight are based on the corresponding figures for the amount comprised in the stream (S1).

In step e), a stream (S3) comprising at least 70% by weight, preferably at least 90% by weight, of phase (B) is discharged from the coalescing device (KV). The stream (S2) particularly preferably does not comprise any phase (A) or comprises only a small amount (<1% by weight) of phase (A). The above figures in % by weight are based on the corresponding figures for the amount comprised in the stream (S1).

The stream (S1) provided in step a) is preferably obtained from a phase separation unit located upstream of the coalescing device (KV). This phase separation unit is preferably a phase separator.

Preference is given to using a coalescing filter as coalescing device (KV). If a knitted fabric is used as coalescing device (KV), the knitted fabric is preferably preceded by a phase separation unit which does not comprise a knitted fabric.

Furthermore, preference is given to a reaction apparatus or a cascade of reaction apparatuses being located upstream (in turn) of the phase separation unit. This reaction apparatus or cascade of reaction apparatuses preferably comprise(s) apparatuses which are suitable for carrying out an isomerization of hydrocarbons in the presence of at least one ionic liquid as catalyst.

In a preferred embodiment of the present invention, the following additional steps f) to k) which are defined as follows:

f) discharge of a stream (S4) from the reaction apparatus or the cascade of reaction apparatuses, where (S4) comprises a dispersion (D2) in which the phase (B) is dispersed in the phase (A), g) introduction of a stream (S5) comprising at least 70% by weight, preferably at least 90% by weight, of the phase (B) into the stream (S4), where the stream (S5) is recirculated from step k) and the streams (S4) and (S5) are preferably mixed by means of a stirrer or a static mixer, h) to form a stream (S6) comprising a dispersion (D1) in which the phase (A) is dispersed in the phase (B), i) introduction of the stream (S6) into the phase separation unit located upstream of the coalescing device (KV), j) separation of the stream (S6) in the phase separation unit into a stream (S1) as per step a) and a stream (S7) comprising at least 70% by weight, preferably at least 90% by weight, of the phase (A), k) separating-off of part of the stream (S1) and/or part of the stream (S3) as per step e) as stream (S5) and recirculation of the stream (S5) to step g)

are carried out in addition to the above-described steps a) to e).

In the context of the present invention, the stream (S5) introduced into the stream (S4) in step g) is formed by part of the stream (S1). As an alternative, the stream (S5) can also be formed by part of the stream (S3). The stream (S5) can optionally also be formed by different or identical partial amounts of the streams (S1) and (S3). The stream (S5) is preferably formed by part of the stream (S1). For example, from 50 to 90% of the streams (S1) and/or (S3) are separated off as stream (S5) and recirculated to the stream (S4). However, it is also conceivable for larger amounts or even the entire respective streams to be at least temporarily recirculated. The recirculation of parts of the streams (S1) and/or (S3) as stream (S5) and the associated introduction of the stream (S5) into the stream (S4) results in a reversal of the dispersing direction in the stream (S4). Reversal of the dispersing direction means that the stream (S4) comprises a dispersion (D2) in which the phase (B) is dispersed in the phase (A) and that a stream (S6) comprising the dispersion (D1) in which the phase (A) is dispersed in the phase (B) is formed by suitable selection of the amount of the stream (S5) in step g). If a phase separation unit, in particular a phase separator, is located upstream of the coalescing filter (K), the proportion of phase (A) in the dispersion (D1) is further reduced, which has an advantageous effect on the separation performance in the coalescing filter (K).

The introduction of the stream (S5) into the stream (S4) in step g) is preferably effected in a stirring or mixing apparatus in which the stream (S6) as per step h) is formed.

Furthermore, preference is given to the phase ratio of the phase (A) to the phase (B) in the dispersion (D1) comprised in the stream (S6) being ≤3 [kg/kg], preferably ≤0.9 [kg/kg].

Furthermore, preference is given to the stream (S4) being obtained from an isomerization in the presence of an ionic liquid, in particular an isomerization of methylcyclopentane (MCP) to cyclohexane in the presence of an ionic liquid.

Furthermore, preference is given to the separation of stream (S5) from stream (S1) in step k) being effected outside the phase separation unit.

The stream (S7) separated off from the phase separation unit as per step j) and/or the stream (S2) discharged from the coalescing device (KV) in step d), each of which comprise the phase (A), can optionally be recirculated to the reaction apparatus or the cascade of reaction apparatuses. The stream (S7) and/or the stream (S2) can optionally also be recirculated to another point in the process of the invention, for example into a mixing or stirring apparatus in order to control the concentration of the phase (A) in the dispersion (D1).

For the purposes of the present invention, cyclohexane is preferably isolated from the stream (S3). Processes and apparatuses for separating cyclohexane from the stream (S3), especially when the stream is a hydrocarbon mixture, are known to those skilled in the art. Further purification steps (for example scrubbing with an aqueous and/or alkaline phase) which are known to those skilled in the art can optionally also be carried out before the cyclohexane is separated off.

In the FIGURE, the process of the invention (one variant of the above-described preferred embodiment) is illustrated again. According to the FIGURE the process is carried out such that both part of the stream (S1) and part of the stream (S3) are recirculated as stream (S5) to the stream (S4). To aid understanding, the main components of the respective streams are indicated in parentheses underneath. In the case of streams (S1), (S4) and (S6), the dispersing direction of the respective dispersions is also indicated in the respective expression in parentheses, with the arrow showing the dispersing direction. This means that, for example, the dispersion (D2) comprised in the stream (S4) has a phase (B) which is dispersed in the phase (A). In the FIGURE, the introduction of the stream (S5) into the stream (S4) occurs in a mixing apparatus (M). The broken line indicates that the streams (S7) and/or (S2) can optionally also be recirculated to the reaction apparatus or a cascade of reaction apparatuses (R1). In the FIGURE, PT means phase separation unit and K means coalescing filter. However, all other coalescing devices (KV) known to those skilled in the art, for example a knitted fabric, can also be used in place of a coalescing filter (K). However, preference is given to using a coalescing filter (K).

The invention claimed is:

1. A process for separating a phase (A) comprising at least one ionic liquid from a phase (B), wherein the phase (A) has a higher viscosity than the phase (B) and wherein the phase (B) comprises at least one hydrocarbon, which comprises the following steps:
    a) providing a stream (S1) comprising a dispersion (D1) in which the phase (A) is dispersed in the phase (B);
    b) introducing the stream (S1) into a coalescing filter (KV), wherein the inflow rate of the stream (S1) is from 0.05 to 150 kg/(cm²*h) based on the average cross-sectional area of the coalescing filter (KV), wherein the packing density of the coalescing filter (KV) is from 50 to 500 kg/m³, wherein the coalescing filter (KV) contains filter material wherein the filter material comprises at least 50% by weight of acrylic phenolic resin;
    c) separating the phase (A) from the phase (B) in the coalescing filter (KV);
    d) discharging a stream (S2) comprising at least 70% by weight of phase (A) from the coalescing filter (KV); and
    e) discharging a stream (S3) comprising at least 70% by weight of phase (B) from the coalescing filter (KV).

2. The process according to claim 1, wherein the stream (S2) comprises at least 90% by weight of phase (A).

3. The process according to claim 1, wherein the stream (S3) comprises at least 90% by weight of phase (B).

4. The process according to claim 1, wherein:
    i) the inflow rate of the stream (S1) is from 0.5 to 20 kg/(cm² h), based on the average cross-sectional area of the coalescing filter (KV), or
    ii) at least one additional coalescing device is connected to the coalescing filter (KV) in parallel, with the at least one additional coalescing device, and the coalescing filter (KV) being operatable simultaneously or alternately.

5. The process according to claim 1, wherein the inflow rate of the stream (S1) is from 0.5 to 5 kg/(cm²*h), based on the average cross-sectional area of the coalescing filter (KV).

6. The process according to claim 1, wherein;
    i) the coalescing filter (KV) is used without adhesive bonding; or
    ii) the pressure drop over the coalescing filter (KV) is from 0.001 to 1 bar.

7. The process according to claim 6, wherein the pressure drop over the coalescing filter (KV) is from 0.001 to 0.5 bar.

8. The process according to claim 6, wherein the pressure drop over the coalescing filter (KV) is from 0.001 to 0.2 bar.

9. The process according to claim 1, wherein the at least one hydrocarbon comprises cyclohexane.

10. The process according to claim 1, wherein the at least one ionic liquid in the phase (A) is an acidic ionic liquid having the composition $K1Al_nX_{(3n+1)}$, where K1 is a monovalent cation, X is halogen and $1<n<2.5$.

11. The process according to claim 10, wherein K1 comprises an at least partially alkylated ammonium ion or a heterocyclic cation or wherein X is Cl.

12. The process according to claim 1, wherein the dispersion (D1) comprises a maximum of 5% by weight of the phase (A).

13. The process according to claim 1, wherein the stream (S1) is obtained from a phase separation unit which is located upstream of the coalescing filter (KV) and downstream of a reaction apparatus or a cascade of reaction apparatuses.

14. The process according to claim 13, wherein the phase separation unit is a phase separator.

15. The process according to claim 13, further comprising:
    f) discharging a stream (S4) from the reaction apparatus or the cascade of reaction apparatuses, where stream (S4) comprises a dispersion (D2) in which the phase (B) is dispersed in the phase (A);
    g) introducing a stream (S5) comprising at least 70% by weight of the phase (B) into the stream (S4), to form a stream (S6) comprising a dispersion in which the phase (A) is dispersed in the phase (B);
    h) introducing the stream (S6) into the phase separation unit;
    i) separating the stream (S6) in the phase separation unit to provide the stream (S1) and a stream (S7) comprising at least 70% by weight of the phase (A); and
    j) separating part of the stream (S3) to provide the stream (S5) and recirculating the stream (S5) to step g).

16. The process according to claim 15, wherein the stream (S5) comprises at least 90% by weight of the phase (B).

17. The process according to claim 15, wherein the stream (S7) comprises at least 90% by weight of the phase (A).

18. The process according to claim 15, wherein the introduction of the stream (S5) into the stream (S4) in step g) is carried out in a stirring or mixing apparatus to form the stream (S6).

19. The process according to claim 15, wherein the phase ratio of the phase (A) to the phase (B) in the dispersion of the stream (S6) is ≤3 kg/kg.

20. The process according to claim 15, wherein the phase ratio of the phase (A) to the phase (B) in the dispersion of the stream (S6) is ≤0.9 kg/kg.

21. The process according to claim 15, wherein the stream (S4) is obtained from an isomerization.

22. The process according to claim 15, wherein the stream (S4) is obtained from an isomerization in the presence of the at least one ionic liquid.

23. The process according to claim 15, wherein the stream (S4) is obtained from an isomerization of methylcyclopentane (MCP) to cyclohexane in the presence of the at least one ionic liquid.

24. The process according to claim 15, wherein the separating in step j) takes place outside of the phase separation unit.

25. The process according to claim 1, wherein the stream (S3) contains cyclohexane, and further comprising isolating cyclohexane from the stream (S3).

* * * * *